(12) United States Patent
Khan et al.

(10) Patent No.:  US 12,694,965 B2
(45) Date of Patent:      Jul. 28, 2026

(54) THREE-DIMENSIONAL IMAGING AND MACHINE LEARNING SYSTEM FOR IDENTIFYING BONY LANDMARKS USED IN DEVELOPING TREATMENT PROTOCOLS

(71) Applicant: Neuro Spinal Innovation Inc., Mississauga (CA)

(72) Inventors: Aslam Khan, Mississauga (CA); Mayar Abbasi, Pierrefonds (CA)

( * ) Notice:  Subject to any disclaimer, the term of this patent is extended or adjusted under 35 U.S.C. 154(b) by 0 days.

(21) Appl. No.:  18/862,824

(22) PCT Filed:  Feb. 7, 2024

(86) PCT No.:  PCT/CA2024/050152
§ 371 (c)(1),
(2) Date:  Nov. 4, 2024

(87) PCT Pub. No.: WO2024/164075
PCT Pub. Date: Aug. 15, 2024

(65) Prior Publication Data
US 2025/0356985 A1     Nov. 20, 2025

(30) Foreign Application Priority Data
Feb. 7, 2023  (CA) ..................................... 3188843

(51) Int. Cl.
*G16H 20/30*      (2018.01)
*G06F 3/0346*    (2013.01)
(Continued)

(52) U.S. Cl.
CPC ........... *G16H 20/30* (2018.01); *G06F 3/0346* (2013.01); *G06F 3/03545* (2013.01); *G06T 7/73* (2017.01);
(Continued)

(58) Field of Classification Search
CPC ... G16H 20/30; G06F 3/0346; G06F 3/03545; G06T 7/73; G06T 2207/20081; G06T 2207/30201; G06V 10/70; G06V 40/171
(Continued)

(56) References Cited

U.S. PATENT DOCUMENTS

| | | |
|---|---|---|
| 10,733,728 B2 | 8/2020 | Abbasi |
| 10,893,826 B2 | 1/2021 | Khan |

(Continued)

FOREIGN PATENT DOCUMENTS

| | | | |
|---|---|---|---|
| WO | 2020163324 | 8/2020 | |
| WO | WO-2020163324 A1 * | 8/2020 | ............... G06N 5/01 |

OTHER PUBLICATIONS

Jazini et al., Innovations In Spinal Health Care, Journal of the Spinal Research Foundation, Fall 2018, vol. 13, No. 2, https://spinehealth. org/wp-content/uploads/2023/01/SRF-Journal-Fall-2018-WEB-1. pdf (Year: 2018).*
(Continued)

*Primary Examiner* — Joy Chng
(74) *Attorney, Agent, or Firm* — Lamson IP

(57) ABSTRACT

A method of treating the spine of a patient comprising capturing by a three-dimensional imaging and processing system electronic imaging data of at least the head and shoulder of the patient. The electronic imaging data includes at least images collected during rotation and tilting of the head and shoulders of the patient. A processor in electronic communication with the imaging system computes values representing rotational and tilt data of the head and shoulders from the electronic imaging data captured by the imaging system. Alignment data is computed from the stored values and a spinal treatment protocol is output to a
(Continued)

database. The spinal treatment protocol is retrieved from the database and the spine of a patient is treated based on the spinal treatment protocol.

12 Claims, 1 Drawing Sheet

(51) Int. Cl.

| | |
|---|---|
| *G06F 3/0354* | (2013.01) |
| *G06T 7/73* | (2017.01) |
| *G06V 10/70* | (2022.01) |
| *G06V 40/16* | (2022.01) |

(52) U.S. Cl.
CPC ............ *G06V 10/70* (2022.01); *G06V 40/171* (2022.01); *G06T 2207/20081* (2013.01); *G06T 2207/30201* (2013.01)

(58) Field of Classification Search
USPC ........................................................ 705/2–3
See application file for complete search history.

(56) References Cited

U.S. PATENT DOCUMENTS

| | | | |
|---|---|---|---|
| 2016/0073614 A1 | 3/2016 | Lampe | |
| 2019/0139297 A1 | 5/2019 | Chen | |
| 2019/0291723 A1 | 9/2019 | Srivatsa | |
| 2020/0230012 A1* | 7/2020 | Fuhr | A61H 23/00 |
| 2021/0192759 A1* | 6/2021 | Lang | A61B 34/10 |
| 2021/0279967 A1 | 9/2021 | Gernoth | |
| 2024/0252392 A1* | 8/2024 | Khan | A61H 23/0218 |

OTHER PUBLICATIONS

International Search Report, PCT/CA2024/050152. Apr. 29, 2024.5 pages.
Written Opinion of the International Searching Authority PCT/CA2024/050152. Apr. 29, 2024, 5 pages.

* cited by examiner

THREE-DIMENSIONAL IMAGING AND MACHINE LEARNING SYSTEM FOR IDENTIFYING BONY LANDMARKS USED IN DEVELOPING TREATMENT PROTOCOLS

CROSS-REFERENCE TO RELATED APPLICATIONS

This application is a national stage application of PCT/CA2024/050152 having an international filing date of Feb. 2, 2024, which claims the priority benefit of Canadian patent application No. 3,188,843, which is incorporated herein by reference in its entirety.

FIELD

The present technology is directed to a method that can be used to replace X-rays in locating joints and other bony features in a patient. More specifically, it is a method that relies on three-dimensional imaging and subsequent processing of digital data to precisely locate the bony features of interest.

BACKGROUND

For many chiropractic adjustments, the practitioner requires knowledge of the alignment of the patient's spine. Traditionally, x-rays are taken of a patient's spine to determine if any of the vertebrae are misaligned. These measurements are taken around the X, Y, and Z axes of the patient as defined by the Cartesian coordinate system. X-rays are also used in determining the mean axis of rotation, as disclosed in U.S. Pat. No. 10,733,728. An alternative approach is disclosed in United States Patent Application Publication No. 20150305825 where the placement and direction of the impulse is guided by the analysis of a plurality of precisely placed or acquired tomographic images, preferably MRI images. In yet another approach, disclosed in U.S. Pat. No. 10,893,826, system for displaying and collecting biomechanical measurements is provided. The system comprises: an electronic caliper including a bar, two arms slidably mounted on the bar and extending normal therefrom, a display module, and an electronic system housed in the display module and comprising a light emitting diode string of lights, a nine-axis sensor, firmware, a wireless radio, and a power source connector for electronic communication with a power source; and a remote computing device, the wireless radio in communication with the remote computing device. The electronic caliper and method of use thereof is also provided. This system, while very useful suffers the deficiencies of potentially introducing human error, having to contact the patient and having to collect and process the data before determining a treatment protocol.

United States Patent Application Publication No. 20210279967 discloses devices, systems, and methods that generates a three-dimensional (3D) model of an object based on images and tracked positions of a device during acquisition of the images. For example, an example process may include acquiring sensor data during movement of the device in a physical environment including an object, the sensor data including images of a physical environment acquired via a camera on the device, identifying the object in at least some of the images, tracking positions of the device during acquisition of the images based on identifying the object in the at least some of the images, the positions identifying positioning of the device with respect to a coordinate system defined based on a position and orientation of the object, and generating a 3D model of the object based on the images and positions of the device during acquisition of the images. This approach is not accurate enough for identifying and tracking landmarks on a human body.

United States Patent Application Publication No. 20190291723 discloses that pixel image data of a scene is received in which the pixel image data includes a two-dimensional representation of an object in the scene. Point cloud data including three-dimensional point coordinates of a physical object within the scene corresponding to the two-dimensional representation of the object is received. The three-dimensional point coordinates include depth information of the physical object. The point cloud data is mapped to an image plane of the pixel image data to form integrated pixel image data wherein one or more pixels of the pixel image data have depth information integrated therewith. A three-dimensional bounding box is predicted for the object using a convolutional neural network based upon the integrated pixel image data. This approach is not accurate enough for identifying and tracking landmarks on a human body.

United States Patent Application Publication No. 20190139297 discloses technologies that are provided for generating three-dimensional (3D) skeletons of target objects using images of the target objects captured from different viewpoints. Images of an object (such as a person) can be captured from different camera angles. Feature key points of the object can be identified in the captured images. Key points that identify a same feature in separate images can be correlated using truncated epipolar lines. For example, depth information for a key point can be used to truncate an epipolar line that is created using the key point. The correlated feature key points can be used to create 3D feature coordinates for the associated features of the object. A 3D skeleton can be generated using the 3D feature coordinates. One or more 3D models can be mapped to the 3D skeleton and rendered. The rendered one or more 3D models can be displayed on one or more display devices. This approach is not accurate enough for identifying and tracking landmarks on a human body.

United States Patent Application Publication No. 20160073614 discloses a method of diagnosing lameness in quadrupeds utilizing computer vision and a computerized depth perception system to scan quadrupeds, such as sport horses, over time. The method enables a detailed analysis of the quadruped's movement, and changes thereof over time without the need for attaching sensors to the body of the horse or requiring force plates or expensive high-speed cameras. A processing system receives the input of this movement data and utilizes it to make a determination of severity of lameness signals of the animal. The system is inexpensive enough that non-specialists, such as non-veterinary trained quadruped owners, may install the system at an appropriate location such as a horse barn enabling identification of lameness early, to aid in objectively analyzing rehabilitation from injury, and relating changes in gait to performance changes. While this method allows for detection of ambulatory abnormalities it is not accurate enough for identifying and tracking landmarks on a human body.

What is needed is a method of accurately identifying structural features of a patient's body without X-ray images. It would be preferable if landmarks could be identified by imaging one or more of the head, the shoulder and the pelvis. It would be preferable if the method was based on 3D digital images. It would be preferable if it reduced or eliminated human error. It would be preferable if it was touchless. It would be preferable if the data derived from the three-dimensional images could be used to determine a treatment in real time and track the efficacy of the treatment. It would be further preferable if the data could be used to determine biomechanical relationships in the patient.

SUMMARY

The present technology is a method of accurately identifying structural features of a patient's body without X-ray images. Landmarks can be precisely located and identified by imaging one or more of the head, the shoulder and the pelvis. The method is based on three-dimensional digital images and two-dimensional face recognition software. It reduces or eliminates human error. It is touchless. The data derived from the three-dimensional images can be used to determine a treatment in real time and track the efficacy of the treatment. The data can be used to determine biomechanical relationships in the patient.

In one embodiment, a method is provided for determining a spinal treatment protocol for a patient in real time, the method comprising: selecting a three-dimensional imaging system and a two-dimensional face detection system; selecting a processing system; the three-dimensional imaging a system and the processing system identifying bony landmarks including the patient's head and shoulders; the processing system determining an edge of each shoulder; the three dimensional imaging and the processing system determining a position of the bony landmarks during rotating the patient's head and rotating and tilting the patient's shoulders to provide outputs; the processing system processing the outputs; the two-dimensional face detection system detecting facial landmarks and the processing system determining a position of the facial landmarks during titling of the patient's head to provide outputs; and the processing system processing the outputs, wherein the outputs provide a spinal treatment protocol.

The method may further comprise the three-dimensional imaging system and the processing system identifying body landmarks of the patient's pelvis during rotating and tilting of the patient's pelvis to provide outputs, wherein the outputs provide a spinal treatment protocol.

In one embodiment, a method of determining a spinal treatment protocol for a patient in real time is provided, the method comprising: selecting a three-dimensional imaging and processing system; the three-dimensional imaging and processing system identifying bony landmarks including the patient's head and shoulders; the three-dimensional imaging and processing system determining an edge of each shoulder; determining a position of the bony landmarks during at least one of tilting and rotating at least one of the patient's head and shoulders to provide outputs; and the three-dimensional imaging and processing system processing the outputs to provide a spinal treatment protocol.

The method may further comprise delivering the spinal treatment protocol in real time to an impulse treatment device, the impulse treatment device including a stylus.

In the method the providing a spinal treatment protocol may include providing a treatment vector, which defines an orientation of the stylus in three-dimensions in relation to the patient.

In the method the providing a spinal treatment protocol may include providing an impulse protocol.

In another embodiment, a system for determining a spinal treatment protocol for a patient in real time is provided, the system comprising: a three-dimensional camera; a memory which is in electronic communication with the three-dimensional camera; a processor, which is under control of the memory and is configured to process depth, image and inertial data from the three-dimensional camera to provide inputs; a machine learning component, the machine learning component configured to analyze the inputs to provide outputs; and an analytics component, which is configured to provide the spinal treatment protocol from the outputs to an impulse treatment device in real time.

In yet another embodiment, a method of treating a patient in need thereof is provided, the method comprising: selecting a three-dimensional imaging and processing system; the three-dimensional imaging and processing system identifying bony landmarks including the patient's head and shoulders; the three-dimensional imaging and processing system determining an edge of each shoulder; determining a position of the bony landmarks during at least one of tilting and rotating at least one of the patient's head and shoulders to provide outputs; the three-dimensional imaging and processing system processing the outputs to provide a spinal treatment protocol; the three-dimensional imaging and processing system sending the spinal treatment protocol to an impulse treatment device, which includes a stylus; and the impulse treatment device delivering the spinal treatment protocol to the patient in need thereof.

In the method, the providing the spinal treatment protocol may include providing a treatment vector, which defines an orientation of the stylus in three-dimensions in relation to the patient.

In the method, the providing the spinal treatment protocol may include providing an impulse protocol.

FIGURES

DESCRIPTION

Except as otherwise expressly provided, the following rules of interpretation apply to this specification (written description and claims): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, the terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Figure 1:
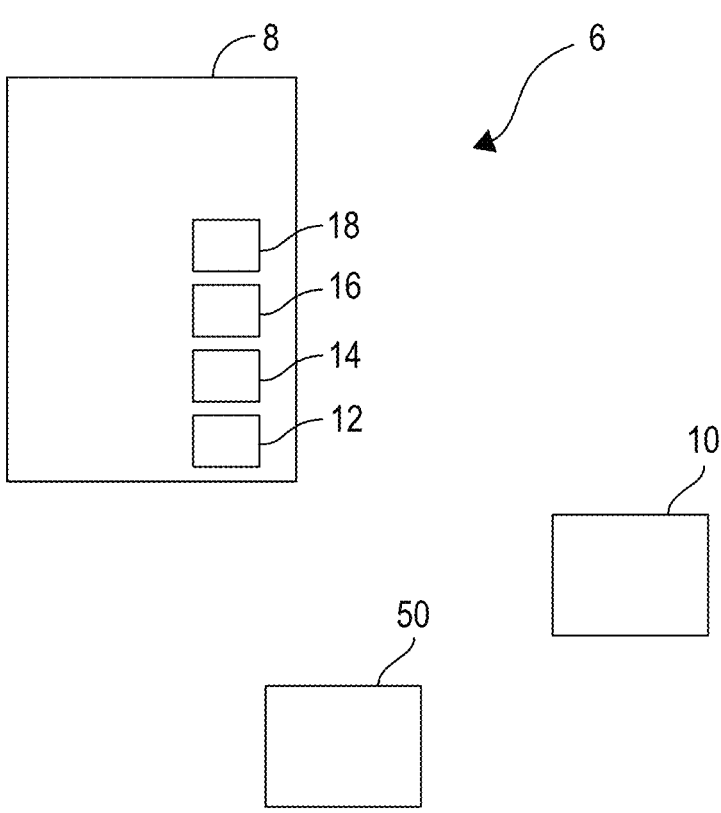
FIG. 1 is a block diagram of the three-dimensional imaging and processing system of the present technology.

As shown in FIG. 1, the three-dimensional imaging and processing system, generally referred to as 6 include an imaging component 8, a machine learning component 10 and an analytics component 50. The imaging component 8 includes a camera 12, which is a three-dimensional camera, which in one embodiment is a Microsoft Kinect Azure® Depth Camera (Kinect), drivers 14 for the depth function for the camera, which in one embodiment are Microsoft Kinect Azure SDK (Kinect SDK) drivers to control the Kinect hardware, and to receive and process all depth sensor, image sensor, and inertial measurement unit (IMU) data, body tracking software 16, which in one embodiment is Microsoft Kinect Body Tracking SDK (KINECT_BT_SDK) to provide (x,y,z) coordinates of human body joints in depth sensor data by the Azure Kinect SDK and face landmark software 18, which in one embodiment is MediaPipe Face Mesh (Mediapipe) to provide red green blue (RGB) images which provide (x,y,z) coordinates of 468 3D face landmarks. The details of the inputs and outputs for the imaging component 8 and the analyses using the machine learning component 10 are conducted as follows.

| Head Analysis | |
|---|---|
| Region Name | Head |
| Inputs: | 2D RGB Image from KINECT_SDK 3D Joint Positions from KINECT_BT_SDK |

| Input + Processing | Output |
|---|---|
| Tilt Calculation | |
| Get Eye Joint Positions from KINECT_BT_SDK | (x, y, z) position of Left Eye and Right Eye in 3D Depth Image |
| Convert (x, y, z) Eye Positions to 2D RGB Coordinates | (x, y) position of Left Eye and Right Eye in 2D RGB Image |
| Extract Head from 2D RGB Image | 2D RGB Image, containing Head of Patient |
| Perform MEDIAPIPE FaceMesh on 2D RGB Image | (x, y) coordinates of 468 face landmarks |
| Using the (x, y) coordinate of landmarks on the Left side of the Head, and corresponding symmetrical landmark on the Right side of the head, calculate the Tilt of the Head | Head Tilt Angle and Side |
| Rotation Calculation | |
| Get Eye Joint Positions from KINECT_BT_SDK | (x, y, z) position of Left Eye and Right Eye in 3D Depth Image |
| Using the (x, y, z) position of the Left and Right Eye, calculate the Angle of the Line in the (x, z) plane connecting the Left and Right Eye. The angle and side of this line represents the head rotation | Head Rotation Angle and Side |

| Shoulder Analysis | |
|---|---|
| Region Name | Shoulder |
| Inputs: | 2D RGB Image from KINECT_SDK 2D Depth Image from KINECT_SDK 3D Joint Positions from KINECT_BT_SDK |

-continued

| Shoulder Analysis | |
| --- | --- |
| Input + Processing | Output |
| Tilt Calculation | |
| Get the Shoulder Joint Positions from KINECT_BT_SDK | (x, y, z) position of Left Shoulder and Right Shoulder in 3D Depth Image |
| Convert (x, y, z) Shoulder Positions to 2D Depth Coordinates | (x, y) depth value of Left Shoulder and Right Shoulder in 2D Depth Image |
| Starting from the (x, y) depth value of each Shoulder on the 2D Depth Image, scan the depth image in the positive y direction (upwards) until the top of shoulder is located, by the distance increases from that of the patient to that of a back wall. | (x, y) position of the top of the shoulder on the 2D Depth Image |
| Convert the (x, y) position of the top of the shoulder in the 2D Depth Image to the corresponding (x, y, z) position in 3D Depth Image | (x, y, z) location of the Top of the Shoulders (Left and Right) in the 3D Depth Image |
| Using the (x, y, z) position of the Left and Right Top of the Shoulder, calculate the Angle of the Line in the (x, y) plane connecting the Left and Right Shoulder Top. The angle and side of this line represents the Shoulder Tilt | Shoulder Tilt Angle and Side |
| Rotation Calculation | |
| Get Clavicle Joint Positions from KINECT_BT_SDK | (x, y, z) position of Left Eye and Right Clavicle in 3D Depth Image |
| Convert (x, y, z) Clavicle Positions to 2D Depth Coordinates | (x, y) depth value of Left Clavicle and Right Clavicle in 2D Depth Image |
| Starting from the (x, y) depth value of the each Clavicle on the 2D Depth Image, scan the depth image in the x direction (towards the corresponding shoulder, left or right) until the left and right side of shoulder (at the y level of the clavicle) is located | (x, y) position of the side of the shoulder on the 2D Depth Image, the same y position as the clavicle |
| Convert the (x, y) position of the side of the shoulder in the 2D Depth Image to the corresponding (x, y, z) position in 3D Depth Image | (x, y, z) location of the Side of the Shoulders (Left and Right) in the 3D Depth Image |
| Using the (x, y, z) position of the Left and Right Side of the Shoulder, calculate the Angle of the Line in the (x, z) plane connecting the Left and Right Side of Shoulder. The angle and side of this line represents the Shoulder rotation | Shoulder Rotation Angle and Side |

| Hip Analysis | | |
| --- | --- | --- |
| Region Name | Hips | |
| Inputs: | 2D RGB Image from KINECT_SDK 3D Joint Positions from KINECT_BT_SDK | |
| Input + Processing | Output | |
| Tilt Calculation | | |
| Get the Hip Joint Positions from KINECT_BT_SDK | (x, y, z) position of Left Hip and Right Hip in 3D Depth Image | |
| Using the (x, y, z) position of the Left and Right Hip, calculate the Angle of the Line in the (x, y) plane connecting the | Hip Tilt Angle and Side | |

| Hip Analysis |
| --- |

| Left and Right Hip. The angle and side of this line represents the Hip Tilt |
| --- |

| Rotation Calculation | |
| --- | --- |
| Input + Processing | Output |
| Get the Hip Joint Positions from KINECT_BT_SDK | (x, y, z) position of Left Hip and Right Hip in 3D Depth Image |
| Using the (x, y, z) position of the Left and Right Hip, calculate the Angle of the Line in the (x, z) plane connecting the Left and Right Hip. The angle and side of this line represents the Hip Rotation | Hip Rotation Angle and Side |

The system 6 has 4 modes of Operation:
1. Cervical Rotation
2. Lateral Bend
3. Anterior
4. Posterior

| Mode Name | Cervical Rotation |
| --- | --- |
| Description | In the Cervical Rotation Mode of operation, the imaging component 8 measures the rotation of the head, as the patient rotates it towards the left and the right. The maximum rotation of each side is measured, and the range of motion is calculated. |
| Software Components | Head Analysis - Rotation |
| Patient Positioning | Patient Stands facing the Camera<br>Patient Rotates head to Left. saves maximum rotation on Left<br>Patient Rotates head to Right. saves maximum rotation on Right |
| Output | Maximum Rotation Left<br>Maximum Rotation Right<br>Range of Motion |

| Mode Name | Lateral Bend |
| --- | --- |
| Description | In the Lateral Bend Mode of operation, imaging component 8 measures the tilt of the head, as the patient tilts it towards the left and the right. The maximum tilt of each side is measured, and the range of motion is calculated |
| Software Components | Head Analysis - Tilt |
| Patient Positioning | Patient Stands facing the Camera<br>Patient Tilts head to Left. saves maximum tilt on Left<br>Patient Tilts head to Right. saves maximum tilt on Right |
| Output | Maximum Tilt Left<br>Maximum Tilt Right<br>Range of Motion |

| Mode Name | Anterior |
| --- | --- |
| Description | In the Anterior Mode of operation, imaging component 8 measures the patient parameters while the patient stands facing the camera, in a neutral position |
| Software Components | Head Analysis - Tilt<br>Head Analysis - Rotation<br>Shoulder Analysis - Tilt<br>Shoulder Analysis - Rotation |
| Patient Positioning | Patient Stands facing the Camera, In Neutral Position |
| Output | Head Tilt (angle, side)<br>Head Rotation (angle, side)<br>Shoulder Tilt (angle, side)<br>Shoulder Rotation (angle, side) |

| Mode Name | Posterior |
| --- | --- |
| Description | In the Posterior Mode of operation, imaging component 8 measures the patient parameters while the patient stands with his posterior facing the camera |
| Software Components | Shoulder Analysis - Tilt Shoulder Analysis - Rotation Hips Analysis - Tilt Hips Analysis - Rotation |
| Patient Positioning | Patient Stands with his/her back facing the Camera, In Neutral Position |
| Output | Shoulder Tilt (angle, side) Shoulder Rotation (angle, side) Hip Tilt (angle, side) Hip Rotation (angle, side) |

Figure 2:
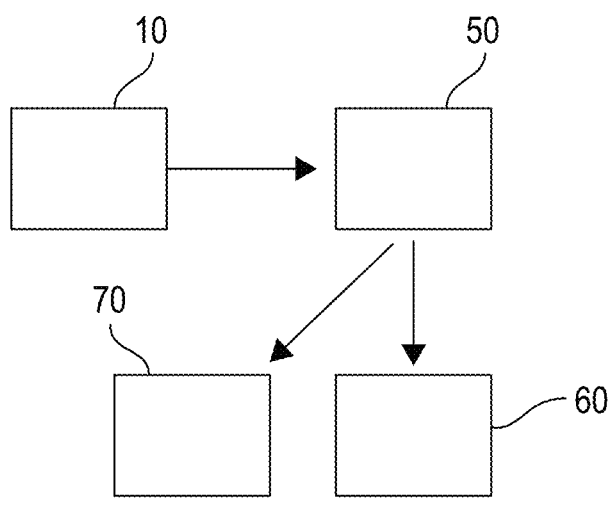
FIG. 2 is a block diagram showing the interface between the three-dimensional imaging and processing system and an impulse treatment device.

As shown in FIG. 2, the outputs from the machine learning component 10 are transferred in real time to the analytics component 50, where the outputs are processed to provide a spinal treatment protocol. The processing involves analysing the outputs to define the alignment of the spine, or specific regions of the spine-one or more of cervical, thoracic and lumbar. Once the alignment is defined, the analytics component defines a treatment. The spinal treatment protocol is transferred in real time to an impulse treatment device 60. The treatment is defined by a list of treatment parameters. The treatment parameters are as follows:

Treatment vector, which defines an orientation of a stylus in the impulse treatment device 60 in three-dimensional space in relation to the position of the patient; and Impulse protocol which includes:

Amplitude (The amplitude of the stylus movement is controlled for frequencies from 5 to up to 40 Hertz (Hz) and 41 Hz to 200 Hz);

Frequency (The stylus is moved such that its tip position follows a sine wave of the selected frequency or a chirp from a start frequency to a stop frequency with an amplitude of up to 3 mm); and Maximum number of periods/cycles at specified frequency.

The outputs from the machine learning component and the treatment from the analytics component 50 is stored in a database 70. The treatment can be obtained from the database on subsequent patient visits.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize or be able to ascertain using no more than routine experimentation, many equivalents to the specific example embodiments specifically described herein. Such equivalents are intended to be encompassed in the scope of the claims, if appended hereto or subsequently filed.

The invention claimed is:

1. A method for treating the spine of a patient, the method comprising:

capturing, by an imaging system comprising at least a three-dimensional camera, electronic imaging data of at least the head and shoulder of the patient, the electronic imaging data including images collected during rotation and tilting of the head and shoulders of the patient;

determining, by a processor in electronic communication with the imaging system, values representing rotational and tilt data of the head and shoulders from the electronic imaging data captured by the imaging system;

storing the determined values representing the rotational and tilt data of the head and shoulder in a memory that is in electronic communication with the three-dimensional camera and the processor;

determining, by the processor, alignment data of one or more of cervical, thoracic and lumbar regions of the spine of the patient by analyzing the values stored in the memory to output alignment data comprising the alignment of one or more of cervical, thoracic and lumbar regions of the spine of the patient;

storing a spinal treatment protocol in a database, the spinal treatment protocol comprising amplitude and frequency data based on the alignment output data;

retrieving the spinal treatment protocol from the database; and treating the spine of the patient by operating a sinusoidal impulse treatment device comprising a stylus to apply sinusoidal wave therapy to the patient via the stylus, the sinusoidal impulse treatment device being operated at an amplitude and frequency selected based on the alignment output data.

2. The method for treating the spine of the patient of claim 1, further comprising capturing, by the imaging system electronic imaging data of the hips of the patient, the electronic imaging data including images collected during rotation and tilting of the hips of the patient.

3. The method for treating the spine of the patient of claim 1, wherein the impulse treatment device comprises a stylus and wherein a treatment vector is input into the impulse treatment device defining an orientation of the stylus in the impulse treatment device in relation to a position of the patient.

4. The method for treating the spine of the patient of claim 1, wherein the rotational and tilt data comprises at least values representing maximum left and right rotational data of the shoulder and a range of motion thereof.

5. The method for treating the spine of the patient of claim 4, wherein the rotational data is an angle of rotation calculated by the processor.

6. The method of claim 1, further comprising capturing two-dimensional face detection image data.

7. A system for treating the spine of a patient, the system comprising:

an imaging sub-system comprising at least a three-dimensional camera for capturing electronic imaging data of at least the head and shoulder of the patient, the electronic imaging data configured for capturing images collected during rotation and tilting of the head and shoulders of the patient;

a processor in electronic communication with the imaging sub-system for determining values representing rotational and tilt data of the head and shoulders from the electronic imaging data captured by the imaging sub-system;

memory for storing the determined values representing the rotational and tilt data of the head and shoulder, the memory being in electronic communication with the three-dimensional camera and the processor;

the processor causing computation of alignment data of one or more of cervical, thoracic and lumbar regions of the spine of the patient by analyzing the values stored in the memory to output alignment data comprising the alignment of one or more of cervical, thoracic and lumbar regions of the spine of the patient; and a database for storing a spinal treatment protocol, the spinal treatment protocol comprising amplitude and frequency data based on the alignment output data, the spinal treatment protocol stored in the database based on the alignment output data, and comprising an amplitude and frequency of a sinusoidal wave using a sinusoidal impulse treatment device for applying to the patient based on data retrieved from the impulse treatment device protocol.

8. The system of claim 7, wherein the imaging system is configured to capture electronic imaging data of the hips of the patient, the electronic imaging data including images collected during rotation and tilting of the hips of the patient.

9. The system of claim 7, wherein the impulse treatment device comprises a stylus and wherein a treatment vector is input into the impulse treatment device defining an orientation of the stylus in the impulse treatment device in relation to a position of the patient.

10. The system of claim 7, wherein the processor is for computing rotational and tilt data from at least values representing maximum left and right rotational data of the shoulder and a range of motion thereof.

11. The system of claim 7, wherein the processor is for computing rotational data that is an angle of rotation.

12. The system of claim 7, wherein the imaging sub-system further comprises a two-dimensional camera for capturing two-dimensional face image data.

* * * * *